(12) United States Patent
Liu et al.

(10) Patent No.: US 11,975,094 B2
(45) Date of Patent: May 7, 2024

(54) THREE-PART MAKEUP REMOVER COMPOSITIONS

(71) Applicant: L'OREAL, Paris (FR)

(72) Inventors: Tianyi Liu, Springfield, PA (US); Hungta Lin, Teaneck, NJ (US)

(73) Assignee: L'OREAL, Paris (FR)

( * ) Notice: Subject to any disclaimer, the term of this patent is extended or adjusted under 35 U.S.C. 154(b) by 44 days.

(21) Appl. No.: 17/340,343

(22) Filed: Jun. 7, 2021

(65) Prior Publication Data

US 2022/0387291 A1    Dec. 8, 2022

(51) Int. Cl.
- *A61Q 1/14* (2006.01)
- *A61K 8/06* (2006.01)
- *A61K 8/898* (2006.01)

(52) U.S. Cl.
CPC .............. *A61K 8/898* (2013.01); *A61K 8/062* (2013.01); *A61K 8/068* (2013.01); *A61Q 1/14* (2013.01); *A61K 2800/87* (2013.01)

(58) Field of Classification Search
CPC .................................... A61K 8/03; A61Q 1/14
See application file for complete search history.

(56) References Cited

U.S. PATENT DOCUMENTS

| 6,162,451 | A | * | 12/2000 | Vanstraceele | ............ | A61Q 1/14 514/846 |
| 6,200,579 | B1 | | 3/2001 | Picard | | |
| 10,780,029 | B2 | | 9/2020 | Bonner et al. | | |
| 2003/0095990 | A1 | | 5/2003 | Hua et al. | | |
| 2003/0161852 | A1 | | 8/2003 | Miller et al. | | |
| 2006/0275245 | A1 | * | 12/2006 | Decoster | .................. | C11D 1/94 424/70.21 |
| 2019/0142706 | A1 | | 5/2019 | Sverdlove et al. | | |

FOREIGN PATENT DOCUMENTS

| CN | 107737028 A | * | 2/2018 | ............... A61K 8/20 |
| CN | 111686025 A | | 9/2020 | |
| DE | 10200724 A1 | | 7/2003 | |
| EP | 0 827 736 A1 | | 3/1998 | |
| FR | 2 680 686 A1 | | 3/1993 | |
| FR | 3 103 706 A1 | | 6/2021 | |
| WO | WO 02/102327 A1 | | 12/2002 | |
| WO | WO-2010095116 A1 | * | 8/2010 | ............... A61K 8/69 |
| WO | WO 2017/058441 A1 | | 4/2017 | |

OTHER PUBLICATIONS

Preliminary Search Report and Written Opinion dated Apr. 25, 2022, in corresponding France Patent Application No. FR2108432 (English Translation of Category of Cited Documents), 9 pages.
Anonymous: "Make Up Remover", Database GNPD [Online] Mintel; XP055912239, Dec. 20, 2019, Database accession No. 7127151, 3 pages.
International Search Report and Written Opinion issued Sep. 15, 2022 in PCT/US2022/032384, 14 pages.

* cited by examiner

*Primary Examiner* — Robert T. Crow
*Assistant Examiner* — John P Nguyen
(74) *Attorney, Agent, or Firm* — WOMBLE BOND DICKINSON (US) LLP

(57) ABSTRACT

The invention relates to three-part makeup remover compositions comprising (a) a water part; (b) an oil part; and (c) a silicone-in-water emulsion part.

19 Claims, No Drawings

THREE-PART MAKEUP REMOVER COMPOSITIONS

FIELD OF THE INVENTION

The present invention generally relates to three-part makeup remover compositions comprising (a) a water part; (b) an oil part; and (c) a silicone-in-water emulsion part.

DISCUSSION OF THE BACKGROUND

Many cosmetic compositions, including pigmented cosmetics such as foundations, mascaras, lipsticks and eye shadows, have been formulated in an attempt to possess long-wear and transfer-resistance properties upon application. Such properties are typically obtained by incorporating one or more film forming agents into the compositions, such as oil-soluble film formers (or waxes), water-soluble film-formers, or resins (e.g., silicone resins like MQ resins). After application, the film-forming agent(s) form a film on the keratinous material to which the composition has been applied to provide long wear and/or transfer-resistance properties. However, such compositions and resulting films can be difficult to remove, particularly if different types of film forming agents are included in the compositions.

U.S. Pat. No. 6,200,579 (EP827736) is entitled "Use of a two-phase composition for make-up removal of transfer-free make-up compositions" and, according to the abstract, relates to removing an applied make-up of long durability and/or a transfer-free make-up composition from the skin by applying to the skin a composition consisting of an aqueous phase and an oily phase, which are distinct, to remove the make-up or transfer-free make-up.

US 2003/0161852 (DE10200724) is entitled "Cosmetic three-phase systems" and, according to the abstract, relates to three-phase systems comprising a) a polyethylene glycol phase comprising a1) 50-100% by weight of at least one polyethylene glycol and a2) 0-50% by weight of water, b) an oil phase and c) a microemulsion phase comprising c1) the components of the polyethylene glycol phase a), c2) the components of the oil phase b) and c3) at least one surfactant which are thermodynamically stable and are preferably suitable as cosmetic compositions, particularly preferably as bath oils.

US 2003/0095990 (WO2002102327) is entitled "Microemulsion facial washes comprising specific oils" and, according to the abstract, relates to a microemulsion comprising oils having defined cleansing and spreadability and providing superior cleansing, mildness, and good feel relative to conventional, non-microemulsion products.

U.S. Pat. No. 10,780,029 (WO2017058441) is entitled "Triphasic cleansing composition" and, according to the abstract, relates to a cleansing composition, a method of making the cleansing composition and a method of using a cleansing composition, the composition including a first liquid surfactant component; a first solid component, including a plurality of cellulose particles; and a first gaseous component.

There remains a need for improved makeup remover compositions for removing long-wear or transfer-resistant makeup compositions from keratinous materials to which they have been applied, particularly if different types of film forming agents are included in the makeup compositions.

SUMMARY OF THE INVENTION

The present invention relates to three-part makeup remover compositions comprising (a) a water part; (b) an oil part; and (c) a silicone-in-water emulsion part.

The present invention relates to three-part makeup remover compositions comprising (a) a water part comprising water and at least one plasticizing agent; (b) an oil part; and (c) a silicone-in-water emulsion part comprising at least one aminated silicone. Preferably, the oil part is substantially free of, devoid of, or free of silicone oils or volatile silicone oils.

The present invention also relates to methods of removing a makeup composition from keratinous material(s) to which it has been applied ("applied makeup composition") by applying a composition of the present invention to the applied makeup composition, and removing the applied makeup composition from the keratinous material.

The present invention also relates to methods of applying compositions of the present invention to an applied makeup composition comprising mixing or blending the composition to form a mixed composition so that the visually distinct/separate parts of the composition are temporarily mingled so that they are temporarily visually indistinct/unseparated, and applying the mixed composition to the applied makeup composition. During or subsequent to application of the mixed composition to the applied makeup composition, the applied makeup composition can be removed from the keratinous material.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, an item of clothing or the skin. Transfer resistance may be evaluated by any method known in the art for evaluating such. For example, transfer resistance of a composition may be evaluated by a modified "kiss" test or material transfer test. This test may involve application of the composition to human keratin material such as skin, eyelashes or lips, followed by rubbing a material, for example, a sheet of paper or cotton ball, against the skin, eyelashes or lips after expiration of a certain amount of time following application, such as 2 minutes after application. Similarly, transfer resistance of a composition may be evaluated by the amount of product transferred from a wearer to any other substrate, such as transfer from the skin, eyelashes or lips of an individual to an article of clothing when putting on the clothing after the expiration of a certain amount of time following application of the composition to the skin, eyelashes or lips. The amount of composition transferred to the substrate (e.g., clothing, paper or cotton ball) may then be evaluated and compared. For example, a composition may be transfer resistant if a majority of the product is left on the wearer's skin, eyelashes or lips. Further, the amount transferred may be compared with that transferred by other compositions, such as commercially available compositions. In a preferred embodiment of the present invention, little or no composition is transferred to the substrate from the skin, eyelashes or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to skin, eyelashes or lips and evaluating the color of the composition after an extended period of time. For example, the color of a composition may be evaluated immediately following application to skin, eyelashes or lips and these characteristics may then be re-evaluated and compared after a certain amount of time such as after 24 hours or 36 hours. Further, these characteristics may be evaluated with respect to other compositions, such as commercially available compositions.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

"Low-water-content" means the compositions contain less than 6% water (by weight). Preferably, compositions of the present invention comprising the at least one sugar contain less than 5% water, and preferably less than 4% water.

"Anhydrous" means the compositions contain less than 1% water (by weight). Preferably, anhydrous compositions of the present invention comprising the at least one sugar contain less than 0.5% water, and preferably no water.

"Polymer" as used herein means a compound which is made up of at least two monomers.

"Free" or "substantially free" or "devoid of" as it is used herein means that while it is preferred that no amount of the specific component be present in the composition, it is possible to have very small amounts of it in the compositions of the invention provided that these amounts do not materially affect at least one, preferably most, of the advantageous properties of the conditioning compositions of the invention. Thus, for example, "free of triethanolamine (TEA)" means that TEA is omitted from the composition (that is, 0% by weight), "substantially free of TEA" means that TEA is are present in amounts not greater than 1% by weight, and "devoid of TEA" means that TEA is present in amounts not greater than 0.5% by weight, based on the total weight of the composition. The same nomenclature applies for all other ingredients identified throughout the application such as, for example, silicone oils ("free of volatile silicone oils," "substantially free of volatile silicone oils," and "devoid of volatile silicone oils" have meanings consistent with the discussion within this paragraph), even if not specifically discussed for each identified ingredient. Discussed examples of the use of such language are intended to be exemplary, not limiting.

The compositions and methods of the present invention can "comprise," "consist of" or "consist essentially of" the essential elements and limitations of the invention described herein, as well as any additional or optional ingredients, components, or limitations described herein or otherwise useful. For purposes of the compositions and methods of the present invention where the invention "consists essentially of" the identified ingredients and/or process steps, the "basic and novel property" of such compositions and/or methods is "removability" of an applied makeup composition from the keratinous material to which it has been applied (e.g., skin, eyelashes or lips).

All U.S. patents or patent applications disclosed herein are expressly incorporated by reference in their entirety.

Makeup Remover Compositions

In accordance with the present invention, three-part makeup remover compositions comprising (a) a water part; (b) an oil part; and (c) a silicone-in-water emulsion part are provided. The compositions of the present invention can comprise, consist essentially of or consist of (a) a water part; (b) an oil part; and (c) a silicone-in-water emulsion part.

"Part" as used herein refers to a portion of the composition which is visually distinct from other portions of the composition. "Part" can be thought of, but does not have to be, as being related to a phase, though not in the traditional sense of "phase." Rather, a "part" or "phase" denotes a separate portion of the composition. Preferably, the "parts" form different layers within the composition at rest (for example, prior to mixing), such as oil part layer/silicone-in-water emulsion part layer/water part layer (from top to bottom). The separateness can be determined visually, similar to when oil and vinegar are combined and visually determined to form separate layers. Thus, for example, a "water part" can be an aqueous phase, and an oil part can be an oil phase. The compositions of the present invention, at rest (for example, prior to mixing), have at least three different "parts" or "portions" which are visually distinct/separate from each other and which correspond to a water part, an oil part, and a silicone-in-water emulsion part.

According to preferred embodiments of the present invention, the compositions of the present invention comprise:
  50% to 95% by weight, preferably 75% to 90% by weight, and preferably 70% to 85% by weight of the (a) water part;
  3% to 25% by weight, preferably 5% to 22% by weight, and preferably 10% to 20% by weight of the (b) oil part; and
  1% to 15% by weight, preferably 2% to 12% by weight, and preferably 3% to 10% by weight of the (c) silicone-in-water emulsion part,
  with all weights being with respect to the total weight of the composition.

(a) Water Part

According to the present invention, the three-part makeup remover compositions comprise (a) a water part. In accordance with the present invention, the water part comprises water and at least one plasticizing agent (plasticizer).

Preferably, water is present in the composition such that water represents from about 50% to about 90% by weight of the total weight of the composition, preferably from about 60% to about 90% of the total weight of the composition, and preferably from about 70% to about 85% of the weight of the total weight of the composition, including all ranges and subranges therebetween, such as, for example, 50% to 65%, 80% to 90%, 75% to 85%, etc.

Preferably, plasticizing agent(s) is/are present in the composition such that plasticizing agent(s) represent from about 0.1% to about 20% by weight, preferably from about 0.25% to about 10% by weight, preferably from about 0.5% to about 5% by weight, of the total weight of the composition, including all ranges and subranges there between, such as, for example, 0.5% to 2%, 1% to 3%, etc.

Generally speaking, plasticizing agents (plasticizers) are additives used to optimize the mechanical properties of films. They tend to reduce the Glass Transition Temperature (Tg) and increase the softness and flexibility of the films. Preferably, suitable plasticizers have a boiling point measured at ambient pressure of less than or equal to 285° C., preferably less than or equal to 270° C., and preferably less than or equal to 250° C. Any plasticizing agent typically found in cosmetic compositions can be used. Examples of suitable plasticizers include, but are not limited to, glycols and their ester derivatives, esters of acids, in particular carboxylic acids, such as citrates, adipates, carbonates, tartrates, phosphates or sebacates, oxyethylenated derivatives, such as oxyethylenated oils, and their mixtures. For example, suitable plasticizing agents include, but are not limited to, diisobutyl adipate, the ester of teributyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, dipropylene glycol n-butyl ether, tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl) acetylcitrate, dibutyl tartrate, camphor, ethyl tosylamide and mixtures thereof. Suitable plasticizers also include, for example, polyurethane plasticizers such as those disclosed in US patent application publication no. 2002/0132915, the entire contents of which is hereby incorporated by reference, as well as polyurethanes like polyurethane 62.

Of course, the water part can also optionally contain additional ingredient(s) compatible with or soluble in water such as, for example, antioxidants, free-radical scavengers, moisturizers, humectants, bleaching agents, liporegulators, anti-acne agents, antiseborrhoeic agents, anti-ageing agents, softeners, anti-wrinkle agents, keratolytic agents, anti-inflammatories, refreshing agents, cicatrizing agents, vascular protective agents, antibacterials, antifungals, antiperspirants, deodorants, skin conditioners, desensitizing agents, immunomodulators and nourishing agents. Specific examples include but are not limited to ascorbic acid and its biologically compatible salts, enzymes, antibiotics, alpha hydroxy acids and their salts, hydroxylated polyacids, sucrose and its derivatives, urea, amino acids, oligopeptides, water-soluble plant and yeast extracts, protein hydrolysates, hyaluronic acid, mucopolysaccharides, vitamins $B_2$, $B_6$, H and PP, panthenol, folic acid, acetylsalicylic acid, allantoin, glycyrrhetic acid, kojic acid and hydroquinone, as well as humectants or moisturizing agents such as, for example, polyhydroxy compounds including but not limited to glycerin and glycols such as, for example, propylene glycol, butylene glycol, dipropylene glycol and diethylene glycol, glycol ethers such as monopropylene, dipropylene and tripropylene glycol alkyl($C_1$-$C_4$)ethers, monoethylene, diethylene and triethylene glycol.

Preferably, the optional water-compatible or water-soluble additional ingredient(s), if present, represent from about 0.1% to about 10% by weight of the total weight of the composition, preferably from about 0.25% to about 5% of the weight of the composition, preferably from about 0.4% to about 2% of the weight of the composition, and preferably from about 0.5% to about 1% of the weight of the composition, including all ranges and subranges therebetween, such as, for example, 0.1% to 0.5%, 5% to 10%, etc.

(b) Oil Part

According to the present invention, the three-part makeup remover compositions comprise (b) an oil part. In accordance with the present invention, the oil part comprises at least one oil.

Preferably, oil(s) is/are present in the composition such that oil represents from about 5% to about 30% by weight of the total weight of the composition, preferably from about 7.5% to about 25% of the total weight of the composition, and preferably from about 10% to about 20% of the weight of the total weight of the composition, including all ranges and subranges therebetween, such as, for example, 2% to 17%, 12% to 22%, 5% to 20%, etc.

Any oils can be used in accordance with the present invention. The oils can be volatile or non-volatile, silicone-based and/or hydrocarbon-based, etc. Thus, for example, the oil part may contain, independently or in combination, volatile silicone oils, non-volatile silicone oils, volatile non-silicone oils and non-volatile non-silicone oils.

Preferably, the compositions of the present invention are substantially free of silicone oils (i.e., contain less than about 1% of silicone oil). Also preferably, the compositions are substantially free of volatile silicone oils (i.e., contain less than about 1% of volatile silicone oil). Also preferably, compositions of the present invention comprise at least one volatile hydrocarbon oil and at least one non-volatile hydrocarbon oil.

The oil part may contain one or more volatile silicone oils. Examples of such volatile silicone oils include linear or cyclic silicone oils having a viscosity at room temperature less than or equal to 6cSt and having from 2 to 7 silicone atoms, these silicones being optionally substituted with alkyl or alkoxy groups of 1 to 10 carbon atoms. Suitable oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |

TABLE 1-continued

| Compound | Flash Point (° C.) | Viscosity (cSt) |
|---|---|---|
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3St) from Dow Corning | 102 | 3 |

Further, a volatile linear silicone oil may be employed in the compositions of the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

The volatility of the solvents/oils can be determined using the evaporation speed as set forth in U.S. Pat. No. 6,338,839.

Examples of other silicone oils that may be used in the invention include non-volatile linear polydimethylsiloxanes (PDMSs), that are liquid at room temperature; polydimethylsiloxanes comprising alkyl, alkoxy or phenyl groups, which are pendent and/or at the end of a silicone chain, these groups each containing from 2 to 24 carbon atoms; phenylsilicones, for instance phenyl trimethicones, phenyl dimethicones, phenyl trimethylsiloxydiphenylsiloxanes, diphenyl dimethicones, diphenyl methyldiphenyl trisiloxanes and 2-phenylethyl trimethylsiloxysilicates.

The oil part may contain one or more non-silicone volatile oils and may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate and their mixtures. Preferably, the volatile non-silicone oils have a flash point of at least 40° C.

TABLE 2

| Compound | Flash Point (° C.) |
|---|---|
| Isododecane | 43 |
| Isohexadecane | 102 |
| Isodecyl Neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

Examples of other non-silicone oils which can be used in the compositions of the present invention include polar oils such as:
hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;
synthetic oils or esters of formula $R_5COOR_6$ in which $R_5$ represents a linear or branched higher fatty acid residue containing from 1 to 40 carbon atoms, including and better still from 7 to 19 carbon atoms, and $R_6$ represents a branched hydrocarbon-based chain containing from 1 to 40 carbon atoms, including and better still from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;
synthetic ethers containing from 10 to 40 carbon atoms; $C_8$ to $C_{26}$ fatty alcohols, for instance oleyl alcohol; and mixtures thereof.

Preferably, the oil part is substantially free of, devoid of, or free of silicone oil as defined above.

Preferably, the oil part is substantially free of, devoid of, or free of volatile silicone oil as defined above.

Of course, the oil part can also optionally contain additional ingredient(s) compatible with or soluble in oil such as, for example, antioxidants, free-radical scavengers, moisturizers, humectants, bleaching agents, liporegulators, anti-acne agents, antiseborrhoeic agents, anti-ageing agents, softeners, anti-wrinkle agents, keratolytic agents, anti-inflammatories, refreshing agents, cicatrizing agents, vascular protective agents, antibacterials, antifungals, antiperspirants, deodorants, skin conditioners, desensitizing agents, immunomodulators and nourishing agents.

Preferably, the optional oil-compatible or oil-soluble additional ingredient(s), if present, represent from about 0.1% to about 10% by weight of the total weight of the composition, preferably from about 0.25% to about 5% of the weight of the composition, preferably from about 0.4% to about 2% of the weight of the composition, and preferably from about 0.5% to about 1% of the weight of the composition, including all ranges and subranges therebetween, such as, for example, 0.1% to 0.5%, 5% to 10%, etc.

(c) Silicone-in-water emulsion part

According to the present invention, the three-part makeup remover compositions comprise (c) a silicone-in-water emulsion part. In accordance with the present invention, the silicone-in-water emulsion part comprises at least one aminated silicone.

The emulsion can contain droplets of any size. However, it is to be understood that, as with any emulsion, smaller and more homogeneous (that is, less diversity of droplet sizes) droplet sizes are preferred because emulsions containing such droplets tend to be more stable.

Preferably, the silicone-in-water emulsion part is a microemulsion. Preferably, average droplet size in the silicone-in-water emulsion part is 1 micron or less, preferably 800 nm or less, preferably 600 nm or less, preferably 500 nm or less, preferably 250 nm or less, and preferably 100 nm or less, including all ranges and subranges therebetween such as, for example, 10 nm to 900 nm, 250 nm to 600 nm, etc. Preferably, measurements are made using a Brookhaven 90Plus particle size analyzer, but can be made via typical or conventional techniques such as using optical microscopy, particularly if particle size is relatively larger.

Preferably, the silicone-in-water emulsion part has at least 85% transparency, preferably at least 90% transparency, and preferably at least 95% transparency, including all ranges and subranges therebetween such as, for example, 85%-95%, 85%-98%, 88%-98%, etc. Preferably, measurements are made using UV visible spectroscopy, with transmittance measured at wavelength(s) of visible light (400-700 nm).

Any suitable means for preparing emulsions can be used to prepare the silicone-in-water emulsion part of the present invention.

The aqueous phase of the emulsion can contain ingredients such as those described above in connection with the (a) water part. The oil phase of the emulsion can contain ingredients such as those described above in connection with the (b) oil part. The silicone-in-water emulsion part also preferably contains at least one emulsifying surfactant (emulsifier) for purposes of stabilizing the silicone-in-water emulsion part as is known in the art.

Such emulsifying surfactants are preferably PPG (polypropylene glycol) or PEG (polyethylene glycol) ethers of fatty alcohols containing from 2 to 20 glycol groups, preferably 5 to 15 glycol groups, and from 8 to 20 carbon atoms, preferably from 12 to 16 carbon atoms such as, for example, trideceth emulsifying surfactants such as trideceth-5, trideceth-10, trideceth-12, etc.

Preferably, the amount of emulsifying surfactant present in the silicone-in-water emulsion part is about 1% or less of the total weight of the composition, preferably about 0.9% or less of the total weight of the composition, preferably about 0.75% or less of the total weight of the composition, and preferably about 0.5% or less of the total weight of the composition, including all ranges and subranges therebetween such as, for example, 0.1% to 0.9%, 0.5% to 0.8%, etc.

Preferably, the silicone phase of the emulsion is substantially free of, devoid of, or free of silicone oil as defined above.

Preferably, the silicone phase of the emulsion is substantially free of, devoid of, or free of volatile silicone oil as defined above.

In accordance with the present invention, the silicone-in-water emulsion part comprises at least one aminated silicone. Suitable aminated silicones are disclosed, for example, in U.S. Pat. No. 9,827,178, the entire contents of which is hereby incorporated by reference.

"Aminated silicone" as used here in means any polyaminosiloxane, i.e. any polysiloxane having at least one primary, secondary, tertiary amine function or a quaternary ammonium group. Suitable aminated silicones include, but are not limited to:

(a) compounds corresponding to the following formula (R1)a(T)3-a-Si[OSi(T)2]n-[OSi(T)b(R1)2-b]m-OSi(T)3-a-(R1)a  (I)

in which:
T is a hydrogen atom, or a phenyl, hydroxyl (—OH), or C1-C8 alkyl radical, and preferably methyl or C1-C8 alkoxy, preferably methoxy,
a denotes the number 0 or an integer from 1 to 3, and preferably 0,
b denotes 0 or 1, and in particular 1,
m and n are numbers such that the sum (n+m) can vary notably from 1 to 2000 and in particular from 50 to 150, with n denoting a number from 0 to 1999 and notably from 49 to 149 and m denoting a number from 1 to 2000, and notably from 1 to 10;
R1 is a monovalent radical of formula —CqH2qL in which q is a number from 2 to 8 and L is an amino group optionally quaternized selected from the groups:
—N(R2)—CH2—CH2—N(R2)2;
—N(R2)2; —N+(R2)3Q—;
—N+(R2)(H)2Q—;
—N+(R2)2HQ—;
—N(R2)—CH2—CH2—N+(R2)(H)$_2$Q—,
in which R2 denotes a hydrogen atom, a phenyl, a benzyl, or a saturated monovalent hydrocarbon radical, for example a C1-C20 alkyl radical, and Q-represents a halide ion such as for example fluoride, chloride, bromide or iodide.

In particular, the aminated silicones corresponding to the definition of formula (I) are selected from the compounds corresponding to the following formula (II):

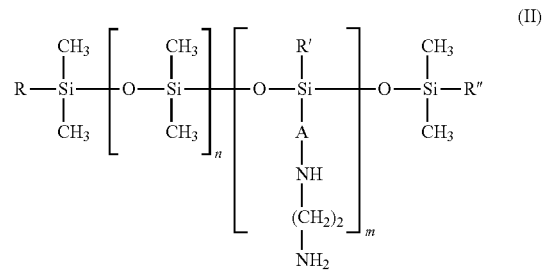

(II)

in which R, R', R", which may be identical or different, denote a C1-C4 alkyl radical, preferably CH3; a C1-C4 alkoxy radical, preferably methoxy; or OH; A represents a linear or branched, C3-C8, preferably C3-C6, alkylene radical; m and n are integers that depend on the molecular weight and whose sum is between 1 and 2000.

Preferably, R, R', R", which may be identical or different, represent a C1-C4 alkyl radical or hydroxyl radical, A represents a C3 alkylene radical, and m and n are such that the weight-average molecular weight of the compound is between about 5000 and 500 000. Compounds of this type are called "amodimethicone" in the CTFA dictionary.

It is also possible that the silicone-in-water emulsion part of the compositions of the present invention can be constituted by a commercially available product. For example, it is possible to use the product sold under the name "DC939" by the company Dow Corning, which comprises, apart from amodimethicone, a cationic emulsifying surfactant, namely trimethylcetylammonium chloride, and a non-ionic emulsifying surfactant of formula: C13H27—(OC2H4)12—OH, known by the CTFA designation "trideceth-12".

Preferably, R, R', R", which may be identical or different, represent a C1-C4 alkoxy radical or hydroxyl radical, at least one of the radicals R or R" is an alkoxy radical and A represents a C3 alkylene radical. The hydroxy/alkoxy molar ratio is preferably between 0.2/1 and 0.4/1 and advantageously equal to 0.3/1. Moreover, m and n are such that the weight-average molecular weight of the compound is between 2000 and 106. More particularly, n is between 0 and 999 and m is between 1 and 1000, the sum of n and m being between 1 and 1000. In this category of compounds, Belsil® ADM 652, marketed by Wacker may be mentioned.

Preferably, R, R", which are different, represent a C1-C4 alkoxy radical or hydroxyl radical, at least one of the radicals R, R" is an alkoxy radical, R' represents a methyl radical and A represents a C3 alkylene radical. The hydroxy/alkoxy molar ratio is preferably between 1/0.8 and 1/1.1, and advantageously is equal to 1/0.95. Moreover, m and n are such that the weight-average molecular weight of the compound is between 2000 and 200000. More particularly, n is between 0 and 999 and m is between 1 and 1000, the sum of n and m being between 1 and 1000. In this category of compounds FluidWR®300, marketed by Wacker may be mentioned.

Preferably, R, R" represent a hydroxyl radical, R' represents a methyl radical and A is a C4-C8, preferably C4, alkylene radical. Moreover, m and n are such that the weight-average molecular weight of the compound is between 2000 and 106. More particularly, n is between 0 and 1999 and m is between 1 and 2000, the sum of n and m being between 1 and 2000. A product of this type is notably marketed under the name DC28299 by Dow Corning. Note that the molecular weight of these silicones is determined by gel permeation chromatography (room temperature, polystyrene standard; columns .mu. styragem; eluent THF; flow of 1 mm/m; inject 200 .mu.l of a 0.5 wt. solution of silicone in THF and use detection by refractometry and with a UV-meter).

A product corresponding to the definition of formula (I) is in particular the polymer called "trimethylsilylamodimethicone" in the CTFA dictionary (7th edition 1997), corresponding to the following formula (III):

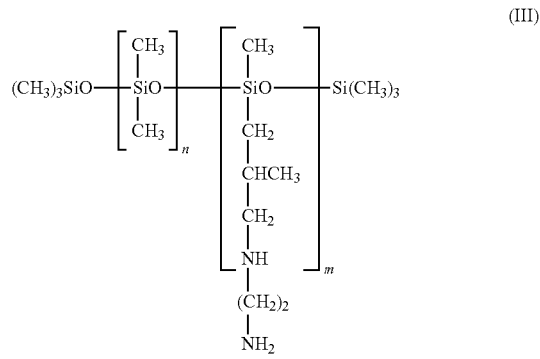

in which n and m have the meanings given above according to formula (I) or (II).

Such compounds are described for example in U.S. Pat. No. 4,563,347 (EP 0095238); a compound of formula (III) is for example sold under the name Q2-8220 by the company OSI;

(b) the compounds corresponding to the following formula (IV):

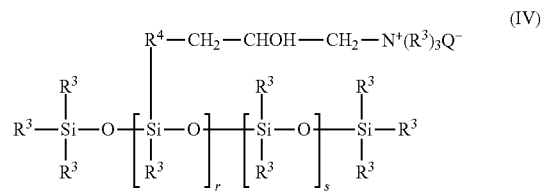

in which:

R3 represents a monovalent C1-C18 hydrocarbon radical, and in particular a C1-C18 alkyl radical or C2-C18 alkenyl radical, for example methyl;

R4 represents a divalent hydrocarbon radical, notably a C1-C18 alkylene radical or a divalent C1-C18, for example C1-C8, alkyleneoxy radical;

Q is a halide ion, notably chloride;

r represents an average random value from 2 to 20 and in particular from 2 to 8;

s represents an average random value from 20 to 200 and in particular from 20 to 50.

Examples of such compounds are described, for example, in U.S. Pat. No. 4,185,087. A compound included in this class is that sold by the company Union Carbide under the name "Ucar Silicone ALE 56";

(c) the quaternary ammonium silicones of formula (V):

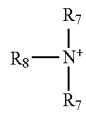 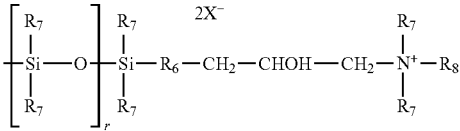

in which:

R7, which may be identical or different, represent a monovalent hydrocarbon radical having from 1 to 18 carbon atoms, and in particular a C1-C18 alkyl radical, a C2-C18 alkenyl radical or a ring comprising 5 or 6 carbon atoms, for example methyl;

R6 represents a divalent hydrocarbon radical, notably a C1-C18 alkylene radical or a divalent C1-C18, for example C1-C8, alkyleneoxy radical joined to the Si by an SiC bond;

R8, which may be identical or different, represent a hydrogen atom, a monovalent hydrocarbon radical having from 1 to 18 carbon atoms, and in particular a C1-C18 alkyl radical, a C2-C18 alkenyl radical, a radical —R6—NHCOR7;

X— is an anion such as a halide ion, notably chloride or a salt of an organic acid (acetate etc.);

r represents an average random value from 2 to 200 and in particular from 5 to 100. These silicones are for example described in application U.S. Pat. No. 5,302,322 (EP0530974). As an example of a compound of formula (V), the product referred to in the CTFA dictionary (1997 Edition) under the name Quaternium 80 such as that offered by the company EVONIK GOLDSCHMIDT under the names ABIL QUAT 3272 or 3474 may be mentioned;

d) the aminated silicones of the following formula:

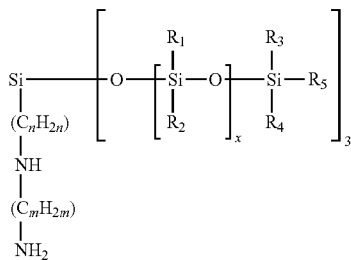

in which: R1, R2, R3 and R4, which may be identical or different, denote a C1-C4 alkyl radical or a phenyl group, R5 denotes a C1-C4 alkyl radical or a hydroxyl group, n is an integer in the range from 1 to 5, m is an integer in the range from 1 to 5, and in which x is selected in such a way that the amine index is between 0.01 and 1 meq/g.

Additional Additives

The compositions of the present invention can also comprise any additive usually used in the field under consideration. For example, non-encapsulated pigments, film forming agents, dispersants, antioxidants, essential oils, preserving agents, fragrances, liposoluble polymers that are dispersible in the medium, fillers, neutralizing agents, silicone elastomers, cosmetic and dermatological oil-soluble active agents such as, for example, emollients, moisturizers, vitamins, anti-wrinkle agents, essential fatty acids, sunscreens, and mixtures thereof can be added. A non-exhaustive listing of such ingredients can be found in U.S. patent application Ser. No. 10/733,467, filed Dec. 12, 2003, the entire contents of which is hereby incorporated by reference. Further examples of suitable additional components can be found in the other references which have been incorporated by reference in this application, including but not limited to the applications from which this application claims priority. Still further examples of such additional ingredients may be found in the *International Cosmetic Ingredient Dictionary and Handbook* (9th ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present).

Needless to say, the composition of the invention should be cosmetically or dermatologically acceptable, i.e., it should contain a non-toxic physiologically acceptable medium and should be able to be applied to the keratin material (such as skin, eyelashes or lips) of human beings. For the purposes of the invention, the expression "cosmetically acceptable" means a composition of pleasant appearance, odor, feel and/or taste.

According to preferred embodiments of the present invention, methods for removing a makeup composition from keratinous material(s) to which it has been applied ("applied makeup composition") by applying a composition of the present invention to the applied makeup composition, and removing the applied makeup composition from the keratinous material are provided. In accordance with this embodiment, the compositions of the present invention are applied topically to the desired area of the keratinous material (e.g., skin, eyelashes or lips) containing applied makeup composition in an amount sufficient to remove the applied makeup composition from the keratinous material (e.g., skin, eyelashes or lips). In this regard, it should be understood that application of the compositions of the present invention to the applied makeup composition does not necessarily result in removal of the applied makeup composition from keratinous material, and that further action may be required such as, for example, rinsing the keratinous material with water (and optionally soap) and/or contacting the keratinous material during or after application of the compositions of the present invention with a cleaning substrate such as a cloth, cottonball, etc.

The present invention also relates to methods of applying compositions of the present invention to an applied makeup composition comprising mixing or blending the composition to form a mixed composition so that the visually distinct/separate parts of the composition are temporarily mingled so that they are temporarily visually indistinct/unseparated, and applying the mixed composition to the applied makeup composition. The composition may be mixed, for example, in a mixing pack or may be mixed by hand (e.g., shaken), if desired. During or subsequent to application of the mixed composition to the applied makeup composition, the applied makeup composition can be removed from the keratinous material, for example as described above.

The present invention also envisages kits and/or prepackaged materials suitable for consumer use containing one or more makeup remover compositions according to the description herein, alone or in combination with makeup products such as foundations, mascaras or lipsticks. The packaging and application device for any subject of the invention may be chosen and manufactured by persons skilled in the art on the basis of their general knowledge, and adapted according to the nature of the composition to be packaged. Indeed, the type of device to be used can be in particular linked to the consistency of the composition, in particular to its viscosity; it can also depend on the nature of the constituents present in the composition, such as the presence of volatile compounds.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example 1—Makeup (Mascara) Remover Composition

The following exemplary three-part makeup remover composition of the present invention can be prepared:

| INGREDIENT | AMOUNT |
| --- | --- |
| AMINATED SILICONE | 0.5-1% |
| HYDROCARBON ESTERS | 5-15% |
| PHENOXYETHANOL | 0.1-1% |
| VOLATILE HYDROCARBON OIL | 5-10% |
| HUMECTANT | 0.1-1% |
| EMULSIFYING SURFACTANT | 0.1-1% |
| WATER | Qs |
| PLASTICIZER | 1-5% |

Example 2—Sample Applied Makeup Composition Removal Procedure/Testing For Eyelashes Apply a pre-determined number of strokes of mascara onto fake lashes. After drying overnight, weigh fake eyelashes with mascara deposited on them.

Then, wet a substrate (e.g., cottonball) with a known amount of makeup remover composition.

Place the fake lashes onto a piece of bioskin and cover with the substrate, and apply a known amount of force onto the substrate. Then, wipe lashes a predetermined number of times with the substrate.

Repeat with a predetermined number of substrates. When finished, allow fake lashes to dry for 1 hour, and weigh.

Then, calculate the amount removed:

% removal=100×(weight of lashes after wiping with remover/weight of mascara before wiping with remover).

Example 3—Comparative Testing: Applied Makeup Composition Removal Procedure/Testing For Eyelashes The procedure from example 2 was repeated, using 30 strokes to apply each mascara composition, 1 gram of makeup remover composition, 4 pieces of cotton round (substrate), 5 wiping strokes per cotton round, and 450 g of force.

The following mascara compositions were tested and compared. These mascara compositions were identical, except for where indicated:

Invention Example 1 (Contained 15% Oil)

(a) water part=triethyl citrate as plasticizer.

(b) silicone-in-water emulsion part=microemulsion containing amodimethicone and trideceth emulsifying surfactants.

(c) oil part=mixture of volatile and non-volatile hydrocarbon oils (isohexadecane, isopropyl myristate, C12-C15 alkyl benzoate)

Comparative Example 1 (No Oil Part)

Comparative Example 2 (No Plasticizer)

Comparative Example 3 (No Silicone-In-Water Emulsion Part)

Comparative Commercial Product 1—Two Phase Product Containing 50% Oil

Comparative Commercial Product 2—Two Phase Product Containing 15%

The results are set forth in the table below:

| Composition | Avg. of Removability |
| --- | --- |
| Comparative Commercial Product 1 | 53.30% |
| Invention Example 1 | 57.92% |
| Comparative Commercial Product 2 | 23.22% |
| Comparative Example 1 | 33.20% |
| Comparative Example 2 | 41.90% |
| Comparative Example 3 | 28.60% |

These results for invention example 1 and comparative examples 1-3 demonstrated that invention example 1 containing plasticizer, a silicone-in-water emulsion with an aminated silicone, and an oil part surprisingly removed makeup (mascara) much more effectively than identical compositions missing only one of these ingredients.

These results for invention example 1 and comparative commercial products 1 and 2 demonstrated that invention example 1 (15% oil) containing plasticizer, a silicone-in-water emulsion with an aminated silicone, and an oil part surprisingly removed makeup (mascara) much more effectively than commercial product 2 containing the same amount of oil, and that invention example 1 was still more effective (about 10%) than comparative commercial product 1 which contained significantly more oil (50%) (and therefore would have been expected to be a much more effective remover than invention example 1 but surprisingly was not).

What is claimed is:

1. A makeup remover composition comprising (a) a water part comprising water and at least one plasticizing agent; (b) an oil part; and (c) a silicone-in-water emulsion part, wherein (a)-(c) are separate layers in the composition.

2. The composition of claim 1, wherein the oil part is substantially free of volatile silicone oils.

3. The composition of claim 1, wherein the oil part is substantially free of silicone oils.

4. The composition of claim 1, wherein the silicone-in-water emulsion part comprises at least one aminated silicone.

5. The composition of claim 1, wherein the silicone-in-water emulsion contains droplets having an average droplet size of 1 micron or less.

6. The composition of claim 1, wherein the silicone-in-water emulsion has a transparency of at least 85%.

7. A kit comprising the composition of claim 1.

8. A method of removing an applied makeup composition from a keratinous material to which it has been applied comprising applying the composition of claim 1 to the applied makeup composition, and removing the applied makeup composition from the keratinous material.

9. The method of claim 8, wherein the makeup composition is a mascara.

10. The method of claim 8, further comprising mixing the composition of claim 1 to form a mixed composition prior to applying the composition to the applied makeup composition.

11. The method of claim 8, wherein removing the applied makeup composition from the keratinous material comprises contacting the keratinous material with a cleaning substrate.

12. The composition of claim 1, wherein the at least one plasticizing agent is at least one ester of a carboxylic acid.

13. The composition of claim 1, wherein the at least one plasticizing agent is at least one ester selected from the group consisting of citrates, adipates, tartrates, and mixtures thereof.

14. The composition of claim 1, wherein the at least one plasticizing agent is a citrate.

15. The composition of claim 1, wherein the at least one plasticizing agent is triethyl citrate.

16. The composition of claim 1, wherein the at least one plasticizing agent is a polyurethane.

17. The composition of claim 1, wherein the at least one plasticizing agent is present in the composition in an amount of from about 0.5% to about 5% by weight with respect to the total weight of the composition.

18. The composition of claim 1, wherein the at least one plasticizing agent is present in the composition in an amount of from about 1% to about 3% by weight with respect to the total weight of the composition.

19. The composition of claim 1, wherein the composition does not contain cyclopentasiloxane.

\* \* \* \* \*